United States Patent
Ortiz et al.

(10) Patent No.: US 7,135,341 B2
(45) Date of Patent: Nov. 14, 2006

(54) REFERENCE CONTROL CONTAINING A NUCLEATED RED BLOOD CELL COMPONENT

(75) Inventors: Nery Ortiz, Miami, FL (US); Sandra Socarras, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 11/094,644

(22) Filed: Mar. 30, 2005

(65) Prior Publication Data

US 2005/0227359 A1    Oct. 13, 2005

Related U.S. Application Data (60) Provisional application No. 60/560,236, filed on Apr. 7, 2004.

(51) Int. Cl.
  *G01N 31/00*    (2006.01)
(52) U.S. Cl. ............... 436/10; 436/8; 436/63; 436/174; 436/175; 436/17; 436/18; 435/2
(58) Field of Classification Search .......... 436/8, 436/10, 63, 164, 172, 174, 175, 17, 18; 435/2
  See application file for complete search history.

(56) References Cited

U.S. PATENT DOCUMENTS

| | | |
|---|---|---|
| 3,873,467 A | 3/1975 | Hunt |
| 4,213,876 A | 7/1980 | Crews et al. |
| 4,264,470 A | 4/1981 | Chastain et al. |
| 4,299,726 A | 11/1981 | Crews et al. |
| 4,358,394 A | 11/1982 | Crews et al. |
| 4,389,490 A | 6/1983 | Crews et al. |
| 4,405,719 A | 9/1983 | Crews et al. |
| 4,704,364 A | 11/1987 | Carver et al. |
| 5,125,737 A | 6/1992 | Rodriguez et al. |
| 5,196,182 A | 3/1993 | Ryan |
| 5,262,327 A | 11/1993 | Ryan |
| 5,320,964 A | 6/1994 | Young et al. |
| 5,460,797 A | 10/1995 | Ryan |
| 5,512,485 A | 4/1996 | Young et al. |
| 5,529,933 A | 6/1996 | Young et al. |
| 5,559,037 A | 9/1996 | Kim et al. |
| 5,811,099 A | 9/1998 | Ryan |
| 5,849,517 A | 12/1998 | Ryan |
| 5,858,790 A | 1/1999 | Kim et al. |
| 5,874,310 A | 2/1999 | Li et al. |
| 5,879,900 A | 3/1999 | Kim et al. |
| 5,917,584 A | 6/1999 | Li et al. |
| 6,146,901 A | 11/2000 | Carver et al. |
| 6,187,590 B1 | 2/2001 | Kim et al. |
| 6,200,500 B1 | 3/2001 | Ryan |
| 6,221,668 B1 | 4/2001 | Ryan et al. |
| 6,399,388 B1 | 6/2002 | Ryan et al. |
| 6,403,377 B1 | 6/2002 | Ryan et al. |
| 6,406,915 B1 | 6/2002 | Ryan et al. |
| 6,410,330 B1 | 6/2002 | Li et al. |
| 6,448,085 B1 | 9/2002 | Wang et al. |
| 6,472,215 B1 | 10/2002 | Huo et al. |
| 6,569,682 B1 | 5/2003 | Elliott et al. |
| 6,573,102 B1 * | 6/2003 | Li et al. ............ 436/17 |
| 6,653,137 B1 | 11/2003 | Ryan |
| 6,673,618 B1 | 1/2004 | Li et al. |
| 6,723,563 B1 | 4/2004 | Ryan |

OTHER PUBLICATIONS

Tsuji, T., et al., "New Rapid Flow Cytometric Method for the Enumeration of Nucleated Red Blood Cells", Cytometry 37:291-301 (1999).
U.S. Appl. No. 11/048,086, filed Feb. 1, 2005, Lopez.

* cited by examiner

*Primary Examiner*—Maureen M. Wallenhorst
(74) *Attorney, Agent, or Firm*—Cuspa Technology Law Associates; Mitchell E. Alter

(57) ABSTRACT

A method of making a reference control containing a nucleated red blood cell component includes providing a blood cell containing a nucleus; treating the blood cell with a treatment solution to alter a nucleus property from a natural value to a target value suitable for simulating nucleated red blood cells on a blood analyzer; and suspending treated blood cell in a suspension medium to form a reference control. The method also includes integrating the nucleated red blood cell component with white blood cell, red blood cell, platelet and reticulocyte components. Further disclosed is a cell treatment composition for altering a nucleus property, which includes a conditioning component, a lytic component for permeating cell membrane, and a fixing component for preserving the cell nucleus. Also disclosed is a method of using the reference control for measurement of nucleated red blood cells on a blood analyzer.

7 Claims, 8 Drawing Sheets

REFERENCE CONTROL CONTAINING A NUCLEATED RED BLOOD CELL COMPONENT

CROSS REFERENCE TO RELATED APPLICATION

This application claims the benefit under 35 USC 119 (e) of the provisional patent application Ser. No. 60/560,236, filed on Apr. 7, 2004, which is herein incorporated by reference in its entirety.

FIELD OF THE INVENTION

The present invention relates to a reference control composition containing a nucleated red blood cell component and the method of making and using the reference control composition for determination of nucleated red blood cells of a blood sample on a blood analyzer.

BACKGROUND OF THE INVENTION

Quality control has long been a necessary and routine procedure in clinical hematology. Accuracy in the counting of various types of blood cells is dependent, in part, upon the use of adequate control products and methods of using the control products. With the numerous types of equipment for particle counting now available, quality control by the use of control products is necessary, since the possibility of an instrument malfunctioning is ever present. The traditional method of maintaining a quality control program for automatic particle counting equipment has consisted of providing fresh human blood as a whole blood standard. However, this fresh blood is usable for only one day, therefore, various manufactured control products which have longer product lifetime have been developed.

Commonly used particles in a control product simulate or approximate the types of particles or cells that are intended to undergo analysis. Consequently, these particles have been frequently referred to as analog particles. The analog particles should be selected or designed so that they have certain characteristics that are similar to those of the particles or cells to be analyzed in the instruments. Exemplary characteristics and parameters include similarities in size, volume, surface characteristics, granularity properties, light scattering properties and fluorescence properties.

Various commercial reference control products are now available, which use various processed or fixed human or animal blood cells as analogs of human blood cells. U.S. Pat. No. 5,512,485 (to Young et al) teaches a hematology control comprising several white blood cell analogs made of processed and fixed animal red blood cells. These fixed red blood cells are fixed at their near native cellular size for simulating specific white blood cell subpopulation in a blood sample. Commercially available hematology controls can also contain red blood cell, platelet, reticulocyte and nucleated red blood cell components.

Nucleated red blood cells (NRBCs), or erythroblasts, are immature red blood cells. They normally occur in the bone marrow but not in peripheral blood. However, in certain diseases such as anemia and leukemia, nucleated red blood cells also occur in peripheral blood. Therefore, it is of clinical importance to measure NRBCs in peripheral blood. In recent years, several detection methods for measuring nucleated red blood cells in a blood sample on a hematology instrument have been reported. U.S. Pat. No. 5,559,037 (to Kim et al.) discloses a method for flow cytometric analysis of nucleated red blood cells and leukocytes. The method uses fluorescence, low angle light scatter and axial light loss measurements to differentiate NRBCs from white blood samples. U.S. Pat. No. 5,879,900 (to Kim et al) further discloses a method of differentiating NRBCs, damaged white blood cells (WBC), WBC and a white blood cell differential in a blood sample by flow cytometry.

U.S. Pat. Nos. 5,874,310 and 5,917,584 (to Li et al) disclose a method of differentiating nucleated red blood cells by measuring two angles of light scatter signals of a blood sample. U.S. Pat. Nos. 5,874,310 and 5,917,584 further disclose a method of differentiating nucleated red blood cells by measuring light scatter and DC impedance signals. U.S. Pat. Nos. 6,410,330 and 6,673,618 (to Li et al) disclose a method of determining NRBC by using DC impedance measurement. U.S. Pat. No. 6,472,215 (to Huo et al) discloses a method of differentiating nucleated red blood cells by an impedance measurement in combination with a three dimensional DC, RF and light scatter measurements.

With the development of the above-referenced detection methods for nucleated red blood cells, several hematology controls containing a nucleated red blood cell component, or NRBC analog, have been reported.

U.S. Pat. Nos. 6,187,590 and 5,858,790 (to Kim et al) disclose a hematology control comprising a nucleated red blood cell (NRBC) analog made of lysed and fixed avian or fish red blood cells, or lysed and fixed human lymphocytes. U.S. Pat. Nos. 6,187,590 and 5,858,790 further disclose the method of preparing the NRBC analog, by lysing avian or fish red blood cells with a lysing reagent for 1 to 5 minutes, followed by fixing nuclei from the cells with a fixative at 60 to 70° C. for up to 10 minutes.

U.S. Pat. Nos. 6,406,915, 6,403,377, 6,399,388, 6,221,668 and 6,200,500 (to Ryan, et al) disclose a hematology control comprising a NRBC analog derived from avian blood cells. The method includes washing avian red blood cells, such as turkey or chicken red blood cells in a buffer solution and fixing the washed cells with glutaraldehyde phosphate solution at room temperature for one day. U.S. Pat. No. 6,448,085 (to Wang et al) discloses a hematology control comprising a nucleated red blood cell (NRBC) analog which is fixed chicken red blood cells obtained from a commercial source.

U.S. Pat. Nos. 6,653,137 and 6,723,563 (to Ryan) disclose methods of making a nucleated red blood cell component for a hematology control by stabilizing blood cells containing a nucleus, or by lysing and removing cytoplasm from blood cells. U.S. Pat. No. 6,723,563 specifically teaches a method of making the nucleated red blood cell component, which comprises the steps of contacting a blood cell which includes a membrane enclosing a nucleus and cytoplasm with a lysing agent for at least 4 hours, removing cytoplasm from within the membrane, but preserving the general structure of the membrane about the nucleus. The method further comprises fixing the blood cells after removing the cytoplasm.

It has been recognized that the nucleated red blood cell analogs produced from different cell sources and processed by different methods can have different properties. For example, the NRBC analog made from lysed and fixed avian blood cells are suitable for fluorescence based measurement methods, but are too small for sizing methods, such as impedance or light scatter measurement methods, for the purpose of simulating human nucleated red blood cells. Furthermore, the nuclei of the stabilized alligator cells without fixation can also be too small when they are analyzed under certain strong lysing conditions used for blood sample analysis on a hematology analyzer. Therefore, it is desirable to have a method of preparing the NRBC analog which enables altering the natural size of cell nucleus of the blood cells used for preparing the analog, to obtain a target size suitable for a predetermined detection domain for simulating human nucleated red blood cells.

In terms of cell property manipulation, U.S. Pat. No. 6,146,901 (to Carver et al) discloses a method for manipulating the optical and electrical properties of a biological particle to achieve selected target values for respective properties. The method includes providing a base biological particle, such as animal red blood cells, having both optical and electrical properties at respective natural values; contacting the particles with a preincubation media which includes a hypotonic buffered solution and a polyhydroxy alcohol to manipulate the optical and electrical properties of the particle; remaining the particle in the preincubation media for an incubation time; subsequently contacting the particle with a primary fixative solution for a period of time. The incubation time and the time in contact with the primary fixative solution are selected to manipulate the respective natural values of the optical and electrical properties of the particle to achieve the target values of the optical and electrical properties. Carver et al's method is used to manipulate the cell properties by leaking a quantity of hemoglobin from the red blood cells without lysing the red blood cells. Carver et al do not teach manipulation or alteration of nucleus properties of a blood cell.

SUMMARY OF THE INVENTION

In one aspect, the present invention is directed to a reference control containing a nucleated red blood cell component. The reference control comprises a nucleated red blood cell component obtained by treating a blood cell that contains a nucleus with a treatment solution to alter a nucleus property from a natural value to a target value suitable for simulating nucleated red blood cells of a blood sample on a blood analyzer; and a suspension medium suitable for delivering said nucleated red blood cell component to said blood analyzer for analysis of said nucleated red blood cells. The nucleus property includes the size, or an optical property of the nucleus. The optical property can be light scatter property, axial light loss property, or fluorescence property of said nucleus upon staining with a fluorescence dye.

The reference control can further comprise a white blood cell component, red blood cell component, platelet component, and reticulocyte component.

In a further aspect, the present invention is directed to a method of making the reference control containing a nucleated red blood cell component. The method comprises the steps of providing a blood cell containing a nucleus; treating said blood cell with a treatment solution to alter a nucleus property from a natural value to a target value suitable for simulating nucleated red blood cells on a blood analyzer, and to preserve said target value; and suspending treated blood cell in a suspension medium to form said reference control.

In another aspect, the present invention is directed to a cell treatment composition for altering a nucleus property. The cell treatment composition comprises a conditioning component; a lytic component for permeating cell membrane, and enabling said cell treatment composition being in contact with said cell nucleus; a fixing component for preserving said cell nucleus; wherein said conditioning component, said lytic component, and said fixing component are present at predetermined respective concentrations to alter a nucleus property from a natural value to a target value. The conditioning component comprises a buffer, and an osmolality adjusting agent. The fixing component is a fixative such as an aldehyde, oxazolidine, alcohol, cyclic urea, or combination thereof. The lytic component comprises a quaternary ammonium surfactant. The cell treatment composition can further comprise one or more non-ionic surfactants.

In yet a further aspect, the present invention is directed to a method of using a reference control containing a nucleated red blood cell component. The method comprises the steps of providing a reference control containing a nucleated red blood cell component obtained by treating a blood cell that contains a nucleus with a treatment solution to alter a nucleus property from a natural value to a target value suitable for simulating nucleated red blood cells of a blood sample; providing a blood analyzer adapted for analyzing said blood cell sample and differentiating nucleated red blood cells from other cell types; passing the control through said blood analyzer for detection of said nucleated red blood cell component; and reporting nucleated red blood cells in said reference control. The differentiation of nucleated red blood cells from other cell types is obtained using impedance, or optical measurement, or combination thereof. The optical measurement can be fluorescence, light scatter, axial light loss measurements, or combination thereof.

DETAILED DESCRIPTION OF THE INVENTION

In one aspect, the present invention provides a reference control composition that contains a nucleated red blood cell (NRBC) component, and a method of preparing the nucleated red blood cell (NRBC) component and the hematology control composition.

The method includes the steps of: providing a blood cell containing a nucleus; treating the blood cell with a treatment solution to alter a nucleus property from a natural value to a target value suitable for simulating nucleated red blood cells of a blood sample on a blood analyzer, and to preserve the target value of the nucleus; and suspending treated blood cell in a suspension medium to form a reference control. For the purpose of the present invention, the nucleated red blood cell component, as well as other cell type components, are also referred to as analogs, for example, NRBC analog. The term "nucleus property" used herein includes, but is not limited to, the size, or an optical property of the nucleus. The optical property can be light scatter property, axial light loss property, or fluorescence property of said nucleus upon staining with a fluorescence dye.

Suitable examples of blood cells suitable for simulating human nucleated red blood cells include various nucleated animal red blood cells and small mammalian white blood cells. More specifically, reptilian, avian and fish red blood cells, such as alligator, shark and salmon red blood cells, and mammalian lymphocytes from whole blood or grown in vitro by a cell line can be used. In one preferred embodiment, alligator red blood cells were used for making the nucleated red blood cell component.

In one embodiment, the method of preparing the NRBC analog using animal nucleated red blood cells comprises following process steps:

1. Collect a quantity of whole blood of a selected animal species which has nucleated red blood cells in an anticoagulant containing container. Centrifuge the whole blood and remove the top layer (including white blood cells, platelets and plasma).
2. Wash the packed nucleated red blood cells with a buffered isotonic wash solution three times.
3. Wash the packed nucleated red blood cells with a suspension medium and re-suspend washed packed cells in the suspension medium. Preferably, the cell count is in a range from about $0.4 \times 10^6$ to about $0.6 \times 10^6$ cell/µl.
4. Treat the re-suspended nucleated red blood cells by adding a predetermined volume of the re-suspended cells to an equal volume of a treatment solution; mix well by inversion to form a cell treatment suspension; and incubate the cell treatment suspension for a treatment period, to alter a nucleus property from a natural value to a target value, and to preserve the target value.
6. Separate the treated cells from the cell treatment suspension by centrifugation.
7. Re-suspend the treated cells in a suspension medium suitable for analysis on a blood analyzer.

One suitable buffered isotonic wash solution is the phosphate buffered saline solution (PBS). Various other cell wash solutions known in the art can also be used.

Suitable examples of suspension medium include phosphate buffered saline solution and an aqueous solution of a plasma substance. As defined herein, an aqueous solution of a plasma substance comprises an aqueous solution of a serum substance, serum substance in combination with a plasma protein and mixtures thereof. As further defined herein, plasma protein comprises one or more of the proteins contained in plasma. Preferably, such plasma proteins comprise albumin, lipoproteins, globulins, fibrinogens and mixtures thereof. These media may contain other ingredients known to those skilled in the art to confer cell stability. Example 1 provides three example formulas of the suspension medium. Preferably, for long term storage of the NRBC analog, the suspension medium contains a relatively higher concentration of protein. Other examples of suitable medium are more fully described in U.S. Pat. Nos. 4,213,876, 4,299,726, 4,358,394, 3,873,467, 4,704,364, 5,320,964, 5,512,485 and 6,569,682 which are herein incorporated by reference in their entirety.

The treatment solution, also referred to as a cell treatment composition, for altering a nucleus property for the purpose of the present invention comprises a conditioning component, a lytic component for permeating cell membrane and enabling the treatment solution to be in contact with the cell nucleus and a fixing component for preserving the treated nucleus.

In one embodiment, the conditioning component comprises a buffer, and an osmolarity adjusting agent. The buffer and osmolarity adjusting agent can be two separate chemicals, each providing a different function. However, the buffer and osmolarity adjusting agent can also be the same chemical to provide both functionalities. For example, when a phosphate buffer is used in the treatment solution, the pair of phosphate salts can provide both buffering and osmolarity adjusting functions.

In one preferred embodiment, the lytic component comprises a quaternary ammonium surfactant represented by following molecular structure:

wherein $R_1$ is an alkyl, alkenyl or alkynyl group having 12 to 16 carbon atoms; $R_2$, $R_3$ and $R_4$ are alkyl groups having 1 to 4 carbon atoms and $X^-$ is chloride or bromide anion.

Furthermore, the treatment solution can also comprise an ethoxylated alkyl phenol having an alkyl group with 6 to 12 carbon atoms, and between about 10 to about 50 ethylene oxide groups. Moreover, the treatment solution can further comprise an ethoxylated alkyl alcohol represented by following molecular structure:

$$R_1—R_2—(CH_2CH_2O)_n—H$$

wherein $R_1$ is an alkyl, alkenyl or alkynyl group having 10 to 22 carbon atoms, $R_2$ is —O—, and n is between 20 and 35.

The fixing component of the treatment solution is a fixative including, but not limited to, an aldehyde, oxazolidine, alcohol, cyclic urea, or the like. Suitable examples include, without limitation, formaldehyde, glutaraldehyde, diazolidinyl urea, imidazolidinyl urea, dimethylol urea, dimethylol-5,5-dimethylhydantoin, 2-bromo-2-nitropropane-1,3-diol; quaternary adamantine; -hydroxymethyl-1-aza-3,7-dioxabicyclo (3.3.0)octane and 5-hydroxymethyl-1-aza-3,7-dioxabicyclo (3.3.0)octane and 5-hydroxypoly-methyleneoxy-methyl-1-aza-3,7-dioxabicyclo (3.3.0) octane, sodium hydroxymethyl glycinate, and mixtures thereof. In a preferred embodiment, an aldehyde fixative, such as paraformaldehyde, formaldehyde or glutaraldehyde is used.

Other fixatives may be used, such as those disclosed in U.S. Pat. Nos. 5,196,182, 5,262,327, 5,460,797, 5,811,099, 5,849,517, 6,221,668, 5,529,933, and 6,187,590, all of which are hereby incorporated by reference.

Example 1 illustrates an example of preparing the nucleated red blood cell component (NRBC analog) using alligator red blood cells. As shown, using the method and the treatment solution of the present invention, the size, optical property, as well as fluorescence property of the treated cell nuclei are altered from their natural values, or properties. Herein the fluorescence property refers to the fluorescence signals measured on a flow cytometer upon staining the nucleated blood cells, or the treated cell nuclei with a nucleic dye. On the other hand, the optical property can be affected by size and granularity of the nuclei. More specifically, the NRBC analog obtained using the specific treatment solution composition shown in Example 1 is smaller in size, more light scattering, and less fluorescent as shown in FIGS. 2A thru 2E, in comparison to the untreated nucleated red blood cells under various measurement conditions.

Example 2 illustrates another example of preparing the NRBC analog using alligator red blood cells, wherein the process steps of preparing the NRBC analogs are the same as in Example 1, however, the treatment solutions are different in terms of the conditioning component. In Examples 1, the conditioning component is a disodium hydrogenphosphate/sodium dihydrogenphosphate buffer system ($Na_2HPO_4/NaH_2PO_4$), and the treatment solution has an osmolarity of 390 mOsm. In Example 2, the conditioning component includes ammonium citrate and tetramisole, and the treatment solution has an osmolarity of 560 mOsm. As shown in FIGS. 4A thru 4E, the obtained NRBC analog using the treatment solution of Example 2 has substantially smaller sizes, and has a stronger fluorescence signal than the analog obtained using the treatment solution used in Example 1.

Although the exact reaction mechanism is not fully understood, it can be appreciated that when in contact with the nucleated red blood cells, the three functional components of the treatment solution act simultaneously on the cells, and the cell nuclei. The lytic component enables permeation of the treatment solution into the cell membrane and allowing the treatment solution in contact with the cell nuclei. The lytic component can further permeate the nucleus membrane. At the same time, the fixing component, in a competing mode, preserves the cell nuclei by fixation. On the other hand, the conditioning component provides a reaction condition with certain pH and osmolarity, which affects the cell and cell nucleus responses to the lytic and fixing components. In combination, such treatment condition has resulted in alterations of nucleus properties, which can be utilized for simulating NRBCs of a blood sample on a blood analyzer.

In a further embodiment, the reference control composition further includes a white blood cell component which simulates a white blood cell (WBC) under a specific detection condition. In the presence of a white blood cell component, a ratio between the NRBC component and the white blood cell component can be used to report the numbers of NRBCs per 100 WBC, which is the same unit used for reporting nucleated red blood cells in a blood sample in clinical laboratories. Preferably, the white blood cell component or analog has properties similar to one major white blood cell subpopulation, such as granulocytes or lymphocytes.

Furthermore, the white blood cell component can include more than one white blood cell subpopulation component or analog, for example, two, three, four or five white blood cell analogs to simulate the white blood cell subpopulations for a differential analysis. Suitable examples of white blood cell analogs include stabilized and fixed mammalian white blood cells, and processed and/or fixed human and animal red blood cells, as known in the art. In one embodiment, the white blood cell analogs can be made from processed goose and alligator red blood cells for differential analysis using a combination of impedance and light scatter measurement, as taught in U.S. Pat. Nos. 5,320,964 and 5,512,485, which are herein incorporated by reference in their entirety. In another embodiment, the white blood cell analogs can be made from processed avian and human red blood cells for differential analysis using an impedance measurement, as taught in U.S. Pat. No. 4,704,364, which is herein incorporated by reference in its entirety. In a further embodiment, the white blood cell analogs can be made from fixed mammalian white blood cells. The mammalian white blood cells are fixed prior to lysing the red blood cells in the whole blood during the preparation of the white blood cell analogs.

Optionally, the mammalian white blood cells and the animal red blood cells can be further treated by contacting with a lipoprotein during the process of preparing the white blood cell analogs. The contact with lipoprotein can occur prior to fixing the white or red blood cells, it can also occur after fixing and during storage in the suspension medium, as taught in U.S. Pat. Nos. 5,320,964, 5,512,485, 6,406,915, 6,403,377, 6,399,388, 6,221,668, and 6,200,500, which are incorporated herein by reference in their entirety.

In another embodiment, the present invention provides a reference control composition which comprises the above described nucleated red blood cell component, a white blood cell component, and additionally a red blood cell component and a platelet component in the suspension medium.

The red blood cell component can be stabilized human or animal red blood cells, preferably, stabilized human red blood cells. The process of making the red blood cell component has been described in detail in U.S. Pat. Nos. 4,299,726 and 4,358,394, which are incorporated by references in their entirety. The platelet component can be stabilized human or animal platelets, or platelet analogs made from other cell types. One suitable example is processed goat red blood cells as the platelet analog, as disclosed in U.S. Pat. Nos. 4,264,470, 4,389,490 and 4,405,719, which are incorporated by references in their entirety.

The red blood cells of a blood sample or the stabilized human red blood cells in the reference control composition are lysed under lysing conditions normally used for preparing a blood sample for the measurement of nucleated red blood cells and white blood cells, and should not be detected in the measurement if the analyzer operates properly. The platelets of a blood sample under the lysing conditions are reduced in size and they are either below the detection threshold for the measurement of nucleated red blood cells, or are separated from the nucleated red blood cells. The platelet analog described above simulates the response of the platelets of a blood sample under the lysing condition. Therefore, the red blood cell component and platelet component in the reference control composition further reflect the response of the control composition to the lysing reagent, as well as the reaction conditions on the instrument. Hence, the reference control composition containing red blood cell and platelet components can provide further information related to instrument operating conditions.

Moreover, the reference control composition containing red blood cell and platelet components can also be used for the red blood cell and platelet measurements, which are commonly performed together with the measurements of the white blood cells and nucleated red blood cells on an automated hematology analyzer.

Optionally, the reference control composition can further comprise a reticulocyte component for the analysis of reticulocytes.

Example 3 illustrates a preparation of a reference control composition containing a nucleated red blood cell component made with the process described in Example 1, a white blood cell component, a red blood cell component and a platelet component.

Example 4 further illustrates a preparation of a reference control composition containing a nucleated red blood cell component, a plurality of white blood cell subpopulation components, a red blood cell component and a platelet component.

The reference control composition containing the prepared nucleated red blood cell component can be utilized for nucleated red blood cell measurement using various measurement methods.

In one embodiment, the present invention provides a method of using the reference control containing the nucleated red blood cell component for the measurement of nucleated red blood cell using a DC impedance measurement. The measurement method and instrumentation used for measuring nucleated red blood cells in a blood sample were described in U.S. Pat. No. 6,410,330, which is herein incorporated by reference in its entirety.

Figure 2A:
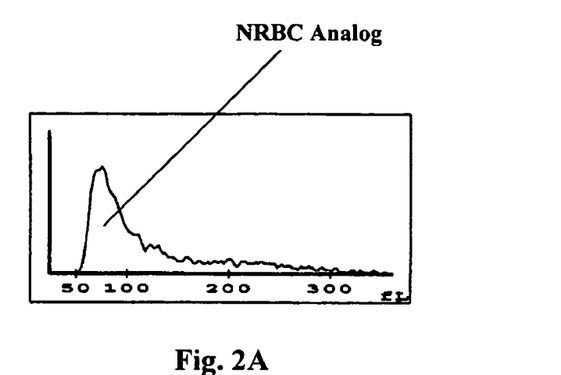
FIG. 2A shows a red blood cell distribution histogram of a NRBC analog made of treated alligator red blood cells using Treatment Solution 1 with the process described in Example 1.
Figure 4A:
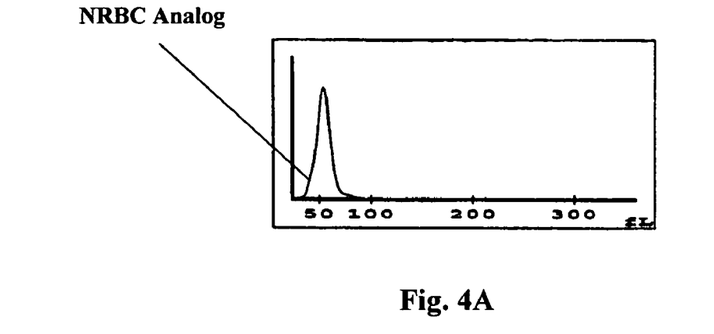
FIG. 4A shows a red blood cell distribution histogram of a NRBC analog made of treated alligator red blood cells using Treatment Solution 2 as described in Example 2.

As shown in FIGS. 2A and 4A, the NRBC analogs made using Treatment Solutions 1 and 2 with the process described in Example 1 simulated the size of nucleated red blood cells of human whole blood samples when processed with a lytic reagent and measured by DC impedance measurement on a hematology analyzer, as described in detail in Example 1.

In another embodiment, the present invention provides a method of using the reference control containing the nucleated red blood cell component for the measurement of nucleated red blood cell using optical measurements. The optical measurements include light scatter measurement, axial light loss measurement, and fluorescence measurement.

The analysis of NRBCs using optical measurement is performed in a focused-flow flow cell. When a particle, such as a blood cell, passes through the aperture of the flow cell, it scatters the incident light in all directions. The light scatter signals can be detected by a light detector at various angles relative to the incident light beam between 0° to 180°. The light scatter signals detected in less than 10° from the incident light are commonly called low angle light scatter. The light scatter signals detected from about 10° to about 70° from the incident light are called medium angle light scatter, and the light scatter signal detected at about 90° of the incident light are called right-angle light scatter, or side scatter. On a flow cytometer the light scatter signals detected at less than 20° from the incident light are commonly referred to as forward light scatter. The characteristics of light scatter signals are affected by the size of a cell, the contents of a cell, and the surface properties of a cell.

Axial light loss (ALL, also known as forward extinction) is generally the decrease in light energy due to a particle passing through a beam of incident light and being detected by a photo-detector. When the beam of incident light strikes a particle, the light is either scattered or absorbed, both of which remove energy from the incident light and the incident beam is attenuated. This attenuation is referred to as extinction. When viewed along the axis of the beam of incident light, it is referred to as axial light loss. Generally ALL signals are detected at an angle from about 0° to about 1° from the incident light. ALL signals are strongly influenced by the size of the cell.

Furthermore, nucleated blood cells upon staining by a nuclear dye can be measured by fluorescence measurement. Depending on the dyes used, the fluorescence signals at several different wavelengths can be utilized for differentiation of nucleated blood cells. It has been found that nucleated red blood cells have different light scattering, axial light loss and fluorescence properties, either significant or minor, from other cell types, which have been utilized for differentiation of this abnormal blood cell population from other cell types.

One suitable example of the measurement method and instrumentation with which the NRBC analog made by the method of the present invention can be utilized as a reference control has been described in detail in U.S. Pat. Nos. 5,874,310 and 5,917,584, which are herein incorporated by reference in their entirety. More specifically, two angles of light scatter signals are used for differentiation of nucleated red blood cells from other cell types. One of the light scatter is a low angle light scatter signal which is less than 10°. The second light scatter angle is a low, a medium or a right-angle light scatter signal. Furthermore, a light scatter measurement in combination of a DC impedance measurement can also be used for measuring nucleated red blood cells.

A further suitable example of the measurement method and instrumentation with which the NRBC analog made by the method of the present invention can be utilized as a reference control has been described in detail in the co-pending patent application Ser. No. 11/048,086, which is herein incorporated by reference in its entirety. In this method, axial light loss and low angle light scatter measurements, preferably from about 3° to 7°, or axial light loss and DC impedance measurements, or combination thereof are used for differentiation of nucleated red blood cells from other cell types.

Figure 2B:
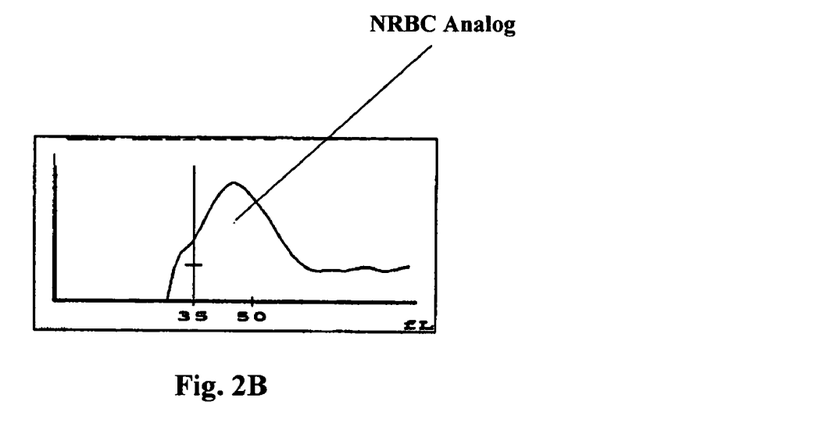
FIG. 2B shows a partially displayed white blood cell distribution histogram of the NRBC analog made of treated alligator red blood cells using Treatment Solution 1 with the process described in Example 1.
Figure 2C:
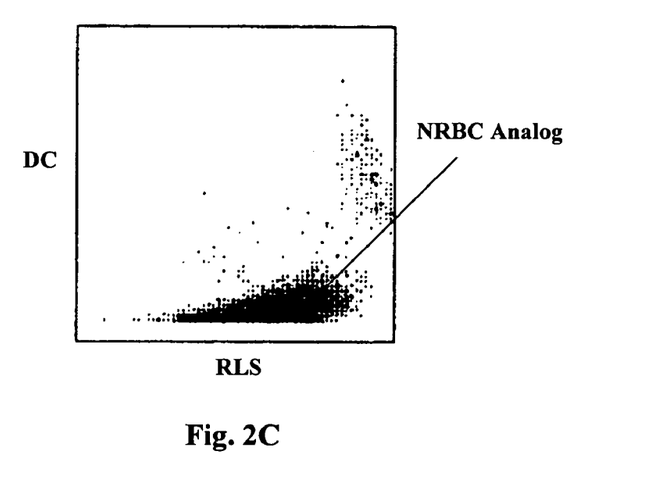
FIG. 2C shows a DC vs. RLS scattergram of the NRBC analog made of treated alligator red blood cells using Treatment Solution 1 with the process described in Example 1.
Figure 2D:
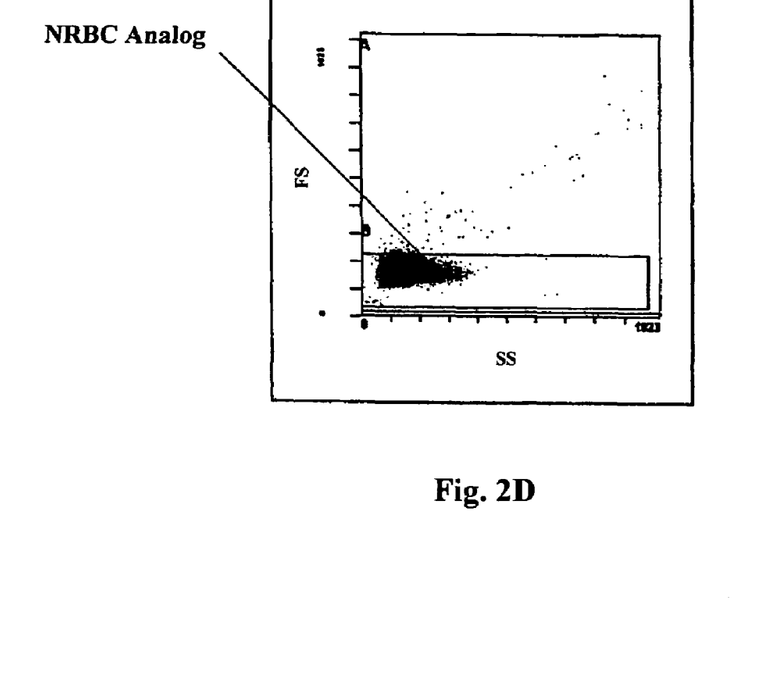
FIG. 2D shows the FS vs. SS scattergram of the NRBC analog made of treated alligator red blood cells using Treatment Solution 1 with the process described in Example 1.
Figure 2E:
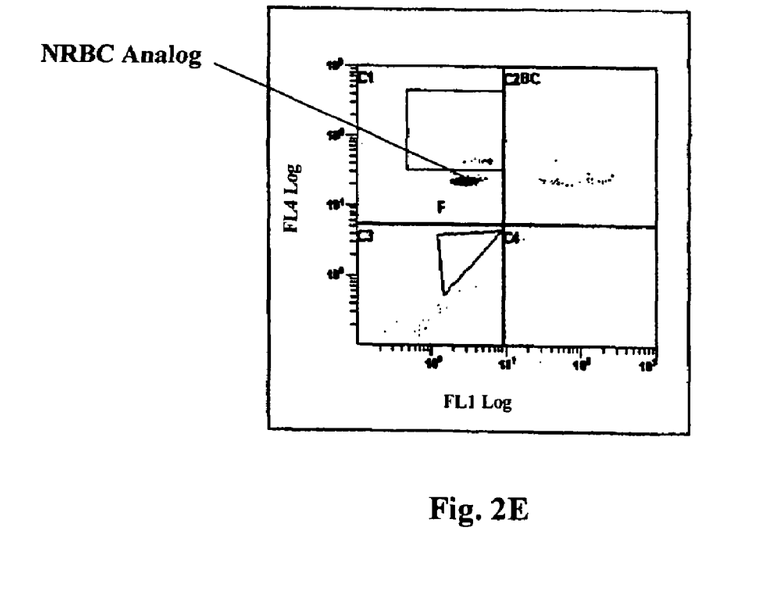
FIG. 2E shows the FL4 vs. FL1 scattergram of the NRBC analog made of treated alligator red blood cells using Treatment Solution 1 with the process described in Example 1.
Figure 3C:
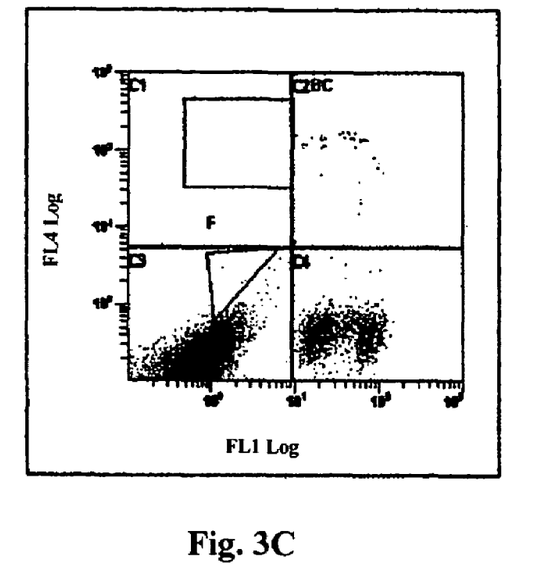
FIG. 3C shows a FL4 vs. FL1 scattergram of a normal whole blood sample.
Figure 3D:
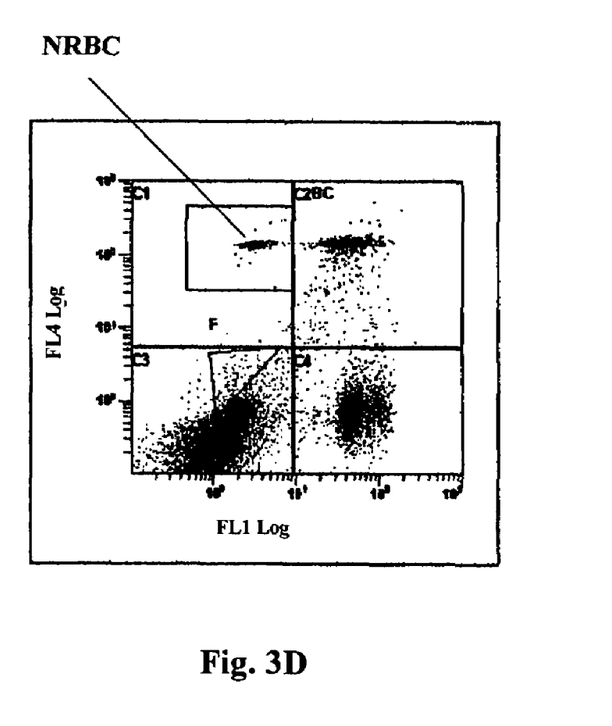
FIG. 3D shows a FL4 vs. FL1 scattergram of a clinical sample containing 13.7 NRBC/100 WBC.
Figure 4B:
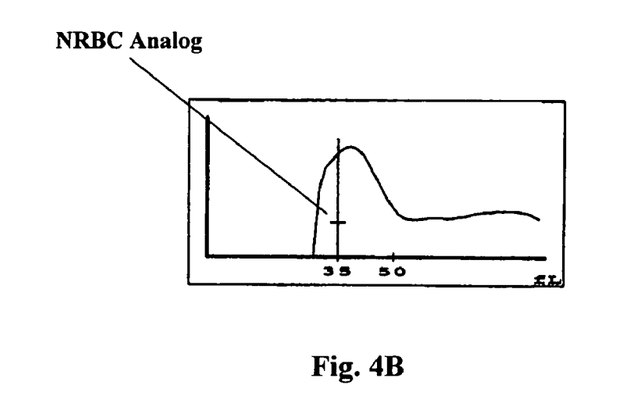
FIG. 4B shows a partially displayed white blood cell distribution histogram of the NRBC analog made of treated alligator red blood cells using Treatment Solution 2 as described in Example 2.
Figure 4C:
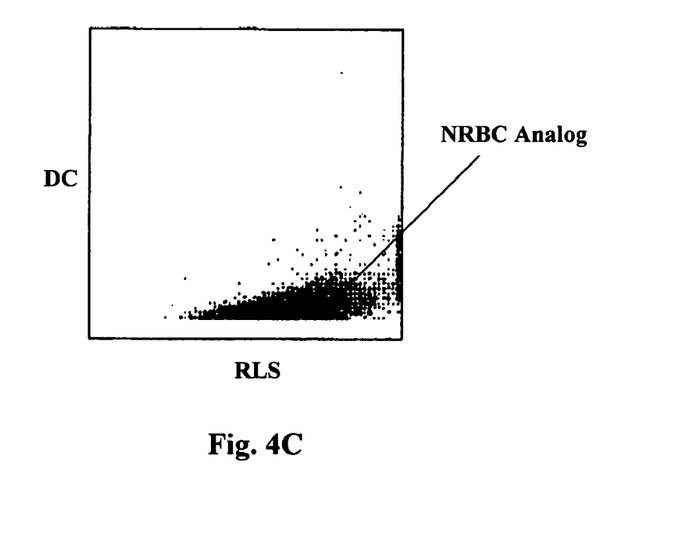
FIG. 4C shows a DC vs. RLS scattergram of the NRBC analog made of treated alligator red blood cells using Treatment Solution 2 with the process described in Example 2.
Figure 4D:
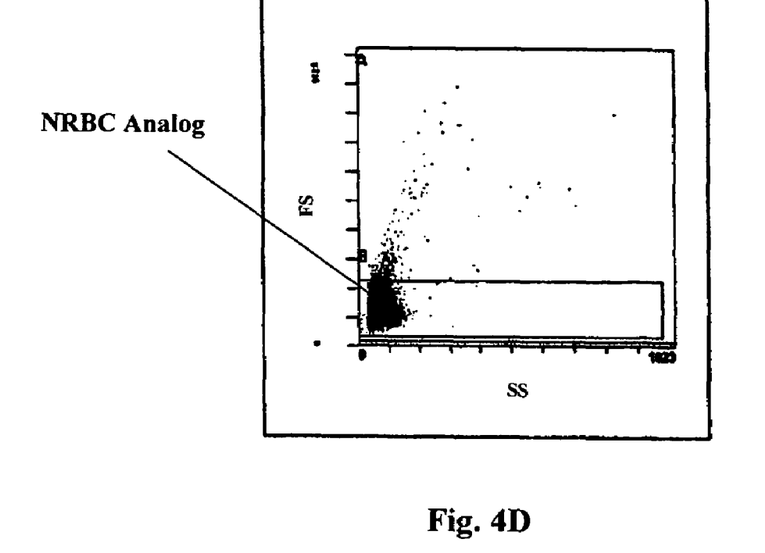
FIG. 4D shows the FS vs. SS scattergram of the NRBC analog made of treated alligator red blood cells using Treatment Solution 2 as described in Example 2.
Figure 4E:
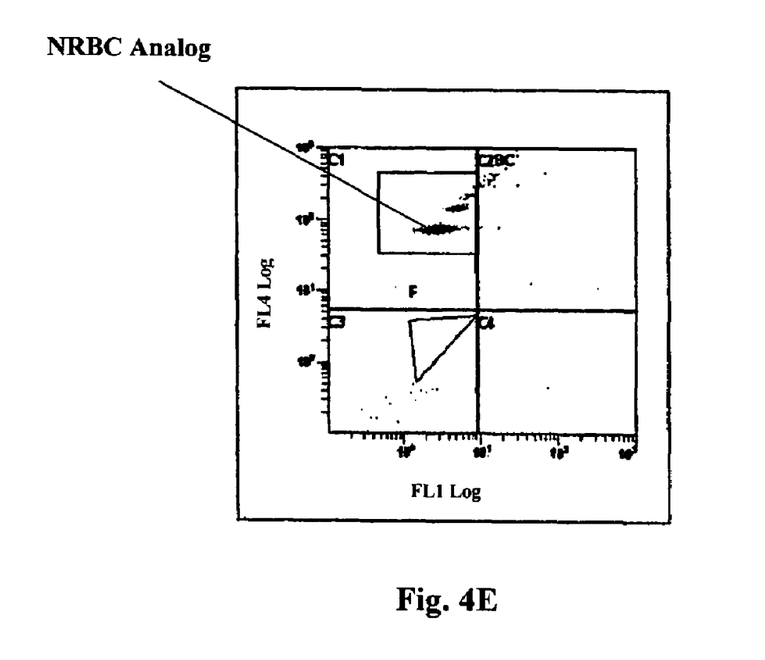
FIG. 4E shows the FL4 vs. FL1 scattergram of the NRBC analog made of treated alligator red blood cells using Treatment Solution 2 as described in Example 2.

Moreover, as shown in FIGS. 2E and 4E, the NRBC analogs made using Treatment Solutions 1 and 2 with the process described in Example 1 can be used to simulate the fluorescence properties of the nucleated red blood cells of human whole blood sample when processed with a reagent system and measured by fluorescence measurements at 525 nm and 675 nm on a flow cytometer. The process of analysis of NRBC in a blood sample on a Coulter FC 500 flow cytometer is described in Example 1 and illustrated in FIGS. 3C and 3D.

In yet another embodiment, the present invention provides a method of using the reference control containing a nucleated red blood cell component for the measurement of nucleated red blood cell using a combination of DC impedance and a VCS measurement method. The measurement method and instrumentation used for the measurement are described in U.S. Pat. No. 6,472,215, which is herein incorporated by reference in its entirety. The term of VCS measurement is referred to a multiple parameter measurement of DC impedance, radio frequency impedance and medium angle light scatter signals, as described in U.S. Pat. No. 5,125,737, which is herein incorporated by reference in its entirety.

As shown in FIGS. 2B, 2C, 4B and 4C, the NRBC analogs made using Treatment Solutions 1 and 2 with the process described in Example 1 can be used to simulate the nucleated red blood cells of human whole blood sample when processed with a reagent system and measured by a combination of DC impedance and VCS measurements on a hematology instrument. The process of analysis of NRBC on a Coulter LH750 hematology analyzer is described in detail in Example 1.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

Preparation of NRBC Analog Using Alligator Red Blood Cells

The following reagent compositions were prepared for the preparation of the NRBC analog.

Phosphate Buffered Saline Solution (PBS)

| | |
|---|---|
| Sodium dihydrogenphosphate: | 0.2 g |
| Disodium hydrogenphosphate 7H$_2$O: | 2.0 g |
| Sodium azide: | 0.1 g |
| Sodium chloride: | 9.4 g |
| Qs to 1 liter with distilled water: | pH approximately 7.4 osmolality 315 to 345 mOsm/kg H$_2$O |

Treatment Solution 1

| | |
|---|---|
| Disodium hydrogenphosphate 7H$_2$O: | 4.781 g |
| Sodium dihydrogenphosphate: | 0.209 g |
| 6% Paraformaldehyde: | 0.6 ml |
| 1% PMSF in DMSO (10 mg/ml) solution: | 0.1 ml |
| Tetradecyltrimethylammonium bromide: | 0.125 g |
| Igepal SS-837 (Rhone-Poulenc): | 0.075 ml |
| Plurofac A38 prill surfactant (BASF Corp.): | 0.02 g |
| Qs to 1 liter with distilled water: | pH approximately 7.6 osmolarity 390 mOsm/kg H$_2$O |

Note:
PSF is α-Toluenesulfonyl fluoride.
Igapal SS-837 is an ethoxylated phenol.
Plurofac A38 is an ethoxylated alkyl alcohol.

Suspension Medium 1

| Component | Range (g/liter) | Preferred (g/liter) |
|---|---|---|
| Xanthine compound | 1–10 | 2–7 |
| Adenosine monophosphate | 0.1–1.0 | 0.2–0.8 |
| Inosine | 0.1–1.0 | 0.2–0.8 |
| pH adjusting agents sufficient to obtain | pH 5.8–6.8 | pH 6.0–6.5 |
| Osmolality adjusters sufficient to obtain | 200–400 mOsm | 250–350 |
| Preservative | effective amount | 2.0–6.0 |
| Qs to 1 liter with distilled water | | |

Suspension Medium 2

| | Preferred (g or ml/liter) |
|---|---|
| Propyl paraben | 0.3 to 1.0 g |
| Methyl paraben | 0.5 to 1.0 g |
| Procaine hydrochloride | 0.1 to 0.5 g |
| Deoxycholic acid | 0.1 to 0.9 g |
| Lactose | 10.0 to 50.0 g |
| Actidione | 0.1 to 0.6 g |
| Trisodium citrate dehydrate | 3.0 to 8.0 g |
| Citric acid monohydrate | 0.3 to 0.9 g |
| Sodium dihydrogenphosphate monohydrate | 0.8 to 2.5 mg |
| Phenergan hydrochloride | 0.1 to 1.0 g |
| Colistimethate, sodium | 0.2 to 0.9 g |
| Penicillin G., sodium | $0.5 \times 10^6$ to $3 \times 10^6$ units |
| Kanamycin sulfate | 0.2 to 0.8 g |
| Neomycin sulfate | 0.2 to 1.0 g |
| 5'-AMP | 0.4 to 1.0 g |
| Adenine | 0.2 to 0.8 g |
| Inosine | 0.4 to 1.0 g |
| Dihydrostreptomycin sulfate | 0.2 to 1.0 g |
| Tetracycline hydrochloride | 0.2 to 1.0 g |
| 30% Bovine albumin | 100 to 350 ml |
| Qs to 1 liter with distilled water | |

Suspension Medium 3

| | Preferred (g or ml/liter) |
|---|---|
| Sodium Chloride | 0.18 g |
| Sodium Hydroxide Pellets | 0.05 g |
| B.S.A. Protease-free | 12.0 g |
| Pluronic F68 | 0.2 g |
| Sodium Phosphate monobasic | 0.18 g |

-continued

| | Preferred (g or ml/liter) |
|---|---|
| EDTA, Di-sodium | 0.02 g |
| Lactose | 2.5 g |
| Citric acid (anhydrous) | 0.032 g |
| Neomycin Sulfate | 0.05 g |
| Adenosine's-monophosphate | 0.05 g |
| TRI-sodium citrate | 0.5 g |
| Sodium penicilin G | 0.08 g |
| Inosine | 0.05 g |
| Procaine HCL | 0.032 g |
| Phenergan HCL | 0.01 g |
| 5-Fluorouracil | 0.1 g |
| MOD-U-CYTE VIII | 20.0 ml |
| Imidazole | 0.025 g |
| Qs to 1 liter with distilled water | pH 6.9–7.1 |
| | osmolarity 330–410 mOsm/kg $H_2O$ |

Process Steps for Preparing NRBC Analog:
1. Collect a quantity of alligator whole blood in an anticoagulant containing container. Centrifuge the alligator whole blood and remove the top layer (including white blood cells, platelets and plasma).
2. Wash the packed alligator red blood cells three times with the phosphate buffered saline solution.
3. Wash the packed alligator red blood cells with the Suspension Medium 1 and re-suspend washed packed cells in the Suspension Medium 1. Preferably, the cell count is in a range from about $0.4 \times 10^6$ to about $0.6 \times 10^6$ cell/μl.
4. Treat the re-suspended alligator red blood cells by adding a predetermined volume of the re-suspended cells to an equal volume of the Treatment Solution 1, and mix well by inversion to form a cell treatment suspension.
5. Incubate the cell treatment suspension at 4° C. overnight.
6. Remove the cell treatment suspension from refrigerator and centrifuge at 1000 rpm for 15 minutes, and remove the supernatant.
7. Re-suspend the treated cells in the Suspension Medium 3 for analysis on a blood analyzer.

The NRBC analog obtained from the above-described treatment process was analyzed on a Coulter® LH750 hematology analyzer (manufactured by Beckman Coulter, Inc., California). The Coulter LH750 hematology analyzer has a RBC bath using three non-focused-flow apertures and a first DC impedance detector for measuring red blood cells; a WBC bath using three non-focused-flow apertures and a second DC impedance detector for measuring white blood cell count, and a 3-part differential analysis of white blood cells and nucleated red blood cells; and a focused-flow flow cell with a VCS detection system for a 5-part differential analysis of white blood cells and nucleated red blood cells. The VCS detection system measures DC impedance, radio frequency impedance and medium angle light scatter signals of a cell passing through the flow cell. Herein the 3-part differential analysis and 5-part differential analysis of white blood cells refer to the differential analysis of white blood cells into three and five subpopulations, respectively.

A blood sample or a reference control was aspirated by the Coulter LH750 hematology analyzer. A first aliquot of the sample was diluted with an isotonic blood diluent, LH700 Series Diluent (product of Beckman Coulter, Inc.), to form a first sample mixture. The first sample mixture was drawn through a set of three apertures by a vacuum source. Each blood cell was measured, as it passed through the apertures by the first DC impedance detector to obtain red blood cell parameters. A second aliquot of the blood sample was diluted with the LH700 Series Diluent, then mixed with a volume of a first lytic reagent, Lyse S® III diff (product of Beckman Coulter, Inc.), to form a second sample mixture. The second sample mixture was drawn through a set of three apertures by a vacuum source, and measured by the second DC detector to obtain white blood cell count, 3-part differential analysis of white blood cells and analysis of nucleated red blood cells. A third aliquot of the sample was mixed with a volume of a second lytic reagent, Erythrolyse™ II, to lyse red blood cells and subsequently mixed with a volume of a stabilizing reagent, StabiLyse™, (both are products of Beckman Coulter, Inc.), to form a third sample mixture. The third sample mixture was delivered to the focused-flow flow cell for a 5-part differential analysis of white blood cells and analysis of nucleated red blood cells. The measurement was performed at a temperature in the range of about 18° to about 28° C. The data obtained from measurements of the second and the third sample mixtures were analyzed collectively to provide the report of the nucleated red blood cells.

Figure 1A:
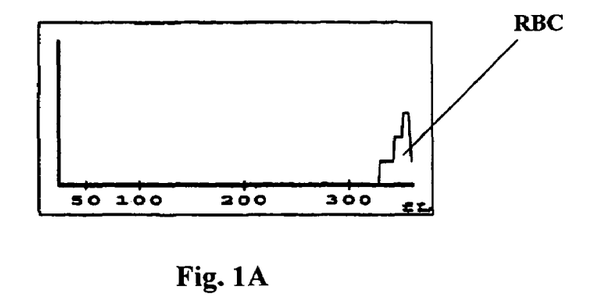
FIG. 1A shows a red blood cell distribution histogram of the washed alligator red blood cells.
Figure 1B:
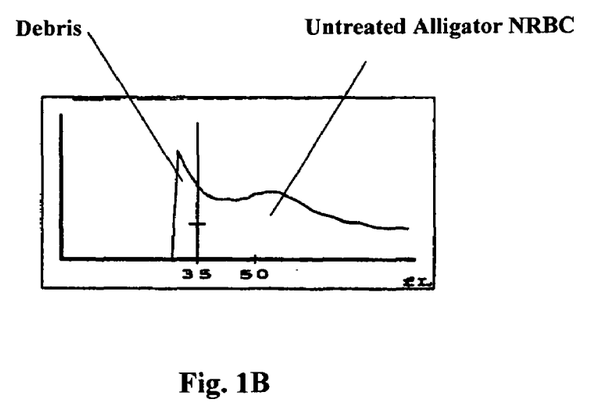
FIG. 1B shows a partially displayed white blood cell distribution histogram of the washed alligator red blood cells.
Figure 1C:
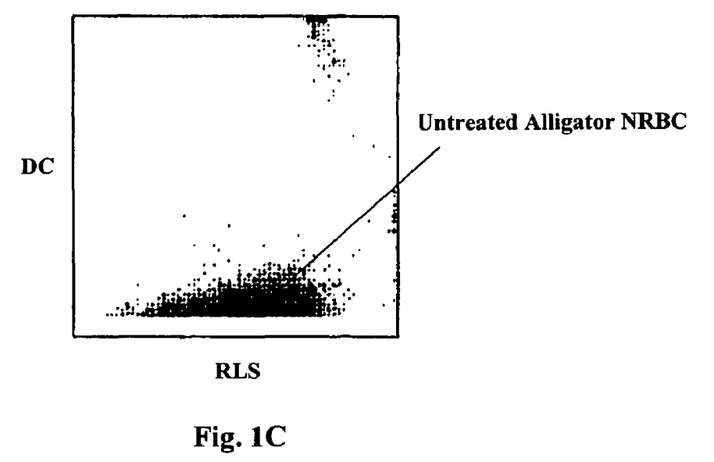
FIG. 1C shows a DC vs. RLS scattergram of the washed alligator red blood cells.

FIG. 1A shows a red blood cell distribution histogram (the first sample mixture in the RBC bath) obtained from washed alligator red blood cells (only processed from Steps 1 to 3, without treatment by Treatment Solution 1). As shown, the washed alligator red blood cells were very large, having a cell size above 300 fl. FIG. 1B shows a partially displayed white blood cell distribution histogram (the second sample mixture in the WBC bath) of the washed alligator red blood cells. As shown, under the lysing condition the nucleated red blood cells measured in the WBC bath were substantially at their nuclear size, having a very broad distribution with a peak at about 55 fl. It is noted that there was a substantial amount of cell debris on the left-most region of the histogram, resulting from the lysing reaction. FIG. 1C shows a DC vs. RLS (rotated light scatter) scattergram of the washed alligator red blood cells. The nucleated red blood cells measured under the lysing condition of the third sample mixture located at the bottom of the DC axis and around the center of the RLS axis. Herein, the RLS is a function of DC and the medium angle light scatter of the VCS detection system.

FIG. 2A shows a red blood cell distribution histogram of a NRBC analog made of treated alligator red blood cells with the process described above using Treatment Solution 1. As shown, the NRBC analog had a size close to the nucleus size of the alligator red blood cells under the lysing condition, which is shown in FIG. 1B. FIG. 2B shows the partially displayed white blood cell distribution histogram of the NRBC analog under the lysing condition in the WBC bath. As shown, the NRBC analog was smaller in size (about 45 fl) and has a narrower and well-defined cell distribution, in comparison to the washed alligator red blood cells. FIG. 2C shows a DC vs. RLS scattergram of the NRBC analog under the lysing condition used for the third aliquot of the blood sample.

Figure 3A:
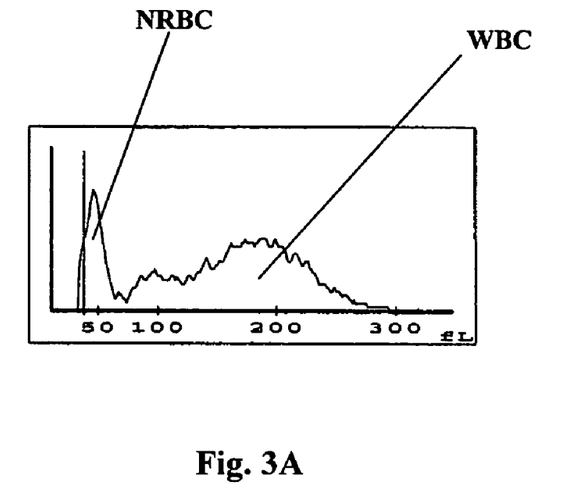
FIG. 3A shows a white blood cell distribution histogram of a clinical sample containing 27 NRBC/100 WBC.
Figure 3B:
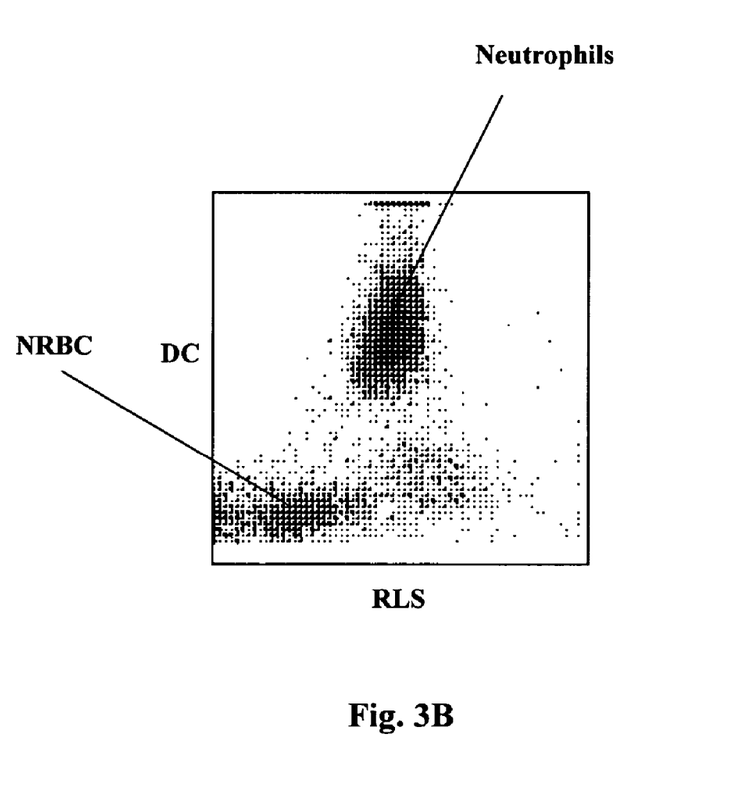
FIG. 3B shows a DC vs. RLS scattergram of the clinical sample of FIG. 3A.

FIG. 3A shows a white blood cell distribution histogram of a clinical blood sample containing 27 NRBC/100 WBC, analyzed on a Coulter LH750 hematology analyzer using the same process described above. FIG. 3B shows the DC vs. RLS scattergram of the clinical sample. It is noted that the display scale of the histogram in FIG. 3A is different from that in FIGS. 1B and 2B, wherein FIG. 3A shows the entire white blood cell distribution, FIGS. 1B and 2B only show the left-most region where the NRBC population located. It is apparent that the NRBC analog shown in FIGS. 2B and 2C was similar in size to human nucleated red blood cells under the same sample analysis conditions.

The NRBC analog obtained from the above-described treatment process was also analyzed on a Coulter FC 500 flow cytometer (manufactured by Beckman Coulter, Inc., California). A 25 µl of a blood sample or a reference control was mixed with 10 µl of FITC labeled anti-CD45 antibody and incubated at room temperature for 30 minutes for labeling the white blood cells. The incubated sample was then mixed with 250 µl of a hypotonic acid lysing reagent (Solution A, which contained a nucleic acid dye) and allowed to stand for 30 seconds to lyse the red blood cells, then mixed with 500 µl of hypertonic alkaline reagent (Solution B) and allowed to stand for 5 minutes at room temperature to restore osmolarity and neutralize the pH and to form a sample mixture. The sample mixture was aspirated by the Coulter FC 500 flow cytometer and measured by the forward and side light scatter detectors, and fluorescence detectors at 525 nm (FL1) and 675 nm (FL4). Solution A comprises 2.10 g/l citric acid monohydrate, 0.56 g/l disodium hydrogenphosphate and 100 mg/l of propidium iodide in de-ionized water, and has a pH of 3.0 and osmolarity of 16 mOsm/kg $H_2O$. Solution B comprises 0.95 g/l sodium dihydrogenphosphate dehydrate, 6.24 g/l disodium hydrogenphosphate and 10.2 g/l of sodium chloride in de-ionized water, and has a pH of 7.5 and osmolarity of 420 mOsm/kg $H_2O$. This analysis method has been described in detail by Tsuji et al, Cytometry 37:291–301, 1999, which is herein incorporated by reference in its entirety.

Figure 1D:
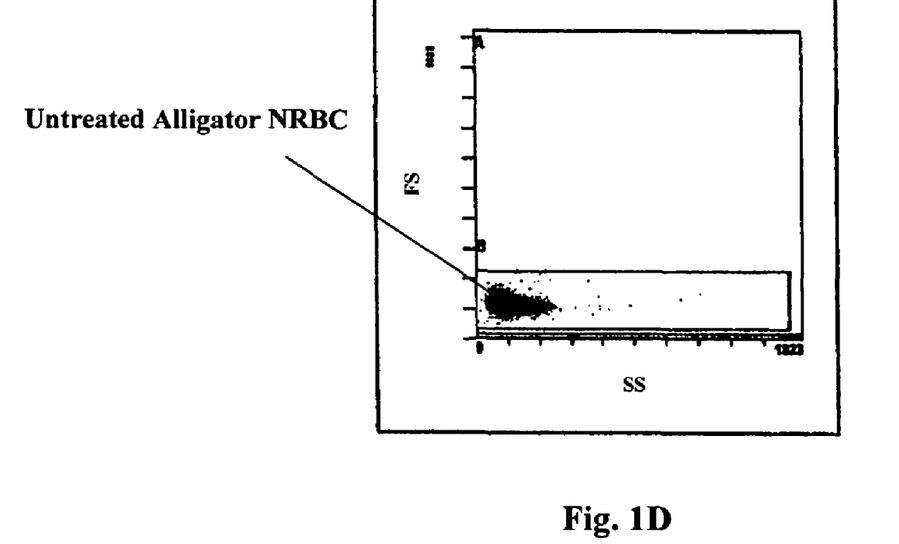
FIG. 1D shows a FS (forward light scatter) vs. SS (side scatter) scattergram of the washed alligator red blood cells.
Figure 1E:
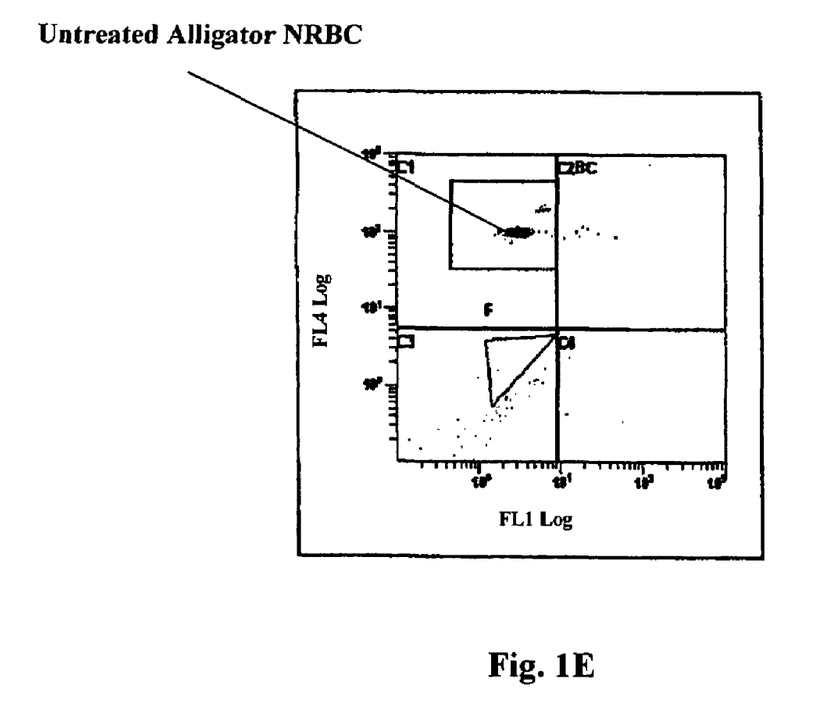
FIG. 1E shows a FL4 vs. FL1 scattergram of the washed alligator red blood cells. It is noted that FL4 and FL1 are in log scale in all fluorescence scattergrams illustrated herein.

FIG. 1D shows a FS (forward light scatter) vs. SS (side scatter) scattergram, and FIG. 1E shows a FL4 (log) vs. FL1 (log) scattergram, of the washed alligator red blood cells (washed as described previously). As shown, the washed alligator red blood cells appear at the bottom left corner of the FS vs SS scattergram, substantially at their nuclear size. In the FL4 (log) vs. FL1 (log) scattergram, the nucleated red blood cells appear in the left upper quadrant. These cells had strong FL4 signals, which are also referred to as $PI^{bright}$. They were CD45$^-$, indicated by their weak FL1 signals.

FIGS. 2D and 2E show the FS vs. SS scattergram and the FL4 vs. FL1 scattergram, respectively, of the NRBC analog made of the treated alligator red blood cells as described above using Treatment Solution 1. As shown, the NRBC analog had increased light scatter signals, particularly the side scatter signal. On the other hand, the NRBC analog had a decreased FL4 signal. It is noted that although the NRBC analog had relatively weaker FL4 signals than the washed alligator red blood cells, the signals were sufficient for simulating the blood samples. Furthermore, the different distribution characteristics of the NRBC analog can be used as a fingerprint of the reference control, which has certain advantages for the instrument to recognize a reference control from a blood sample.

FIGS. 3C and 3D show the FL4 vs. FL1 scattergram of a normal whole blood sample and a clinical sample containing 13.7 NRBC/100 WBC, respectively. As shown in FIG. 3D, the NRBC population located in the left upper quadrant of the scattergram. As shown in FIG. 3C, the normal blood sample did not have a cell population located in this region. Therefore, the NRBC analog made using the process described above can be used for simulating human NRBCs using fluorescent measurements.

The NRBC analog was also made with the above-described process steps except using Suspension Medium 2 in step 3. The analyses on the Coulter LH750 hematology analyzer and the Coulter FC 500 flow cytometer showed that the NRBC analog made with Suspension Medium 2 was similar to those made with Suspension Medium 1.

EXAMPLE 2

Preparation of Nucleated Red Blood Cell Component Using Alligator Red Blood Cells An amount of the same alligator whole blood used in Example 1 was treated with the same process steps described in Example 1, except using Treatment Solution 2 shown below.

Treatment Solution 2

| | |
|---|---|
| Ammonium citrate tribasic: | 19.8 g |
| Tetramisole: | 1.8 g |
| 6% Paraformaldehyde: | 0.6 ml |
| 1% PMSF in DMSO (10 mg/ml) solution: | 0.1 ml |
| Tetradecyltrimethylammonium bromide | 0.125 g |
| Igepal SS-837 (Rhone-Poulenc) | 0.075 ml |
| Plurofac A38 prill surfactant (BASF Corp.) | 0.02 g |
| Qs to 1 liter with distilled water: | pH approximately 5.66 osmolarity 560 mOsm/kg $H_2O$ |

It is noted that the lytic component and the fixing component were the same between Treatment Solution 1 and Treatment Solution 2, however, the conditioning component was different, which resulted in different pH and osmolarity between the two treatment solutions.

The NRBC analog made using Treatment Solution 2 was analyzed on the Coulter LH750 hematology analyzer and the Coulter FC 500 flow cytometer, using the same sample analysis procedure described above.

FIG. 4A shows the red blood cell distribution histogram of the NRBC analog made using Treatment Solution 2. As shown, this NRBC analog had a substantially smaller size than that of the NRBC analog obtained in Example 1. FIG. 4B shows the partially displayed white blood cell distribution histogram of this NRBC analog under the lysing condition in the WBC bath, which was also smaller than that of the NRBC analog obtained in Example 1. However, both NRBC analogs were similar in size to human nucleated red blood cells. FIG. 4C further shows the DC vs. RLS scattergram of the NRBC analog.

FIGS. 4D and 4E show the FS vs. SS and FL4 vs. FL1 scattergrams, respectively, of the NRBC analog of Example 2. As shown in FIG. 4D, the NRBC analog of Example 2 had an increased forward light scatter signal, however, decreased side scatter signals. As shown in FIG. 4E, the NRBC analog had fluorescence signals very similar to that of human nucleated red blood cells.

EXAMPLE 3

Reference Control Composition Containing a Nucleated Red Blood Cell Component, a White Blood Cell Component, and Red Blood Cell and Platelet Components Procedure:
1. Provide a predetermined volume of the Suspension Medium 1 described in Example 1.
2. Add a predetermined amount of stabilized human red blood cells in the suspension medium. The stabilized human red blood cells were prepared following the procedure described in U.S. Pat. Nos. 4,299,726 and 4,358,394.
3. Add a predetermined amount of platelet analog in the suspension medium containing the stabilized human red blood cells. The platelet analog is made of fixed goat red blood cells following the procedure described in U.S. Pat. Nos. 4,264,470, 4,389,490 and 4,405,719.
4. Add a predetermined amount of fixed goose red blood cells as the white blood cell component into the suspension medium containing the stabilized human red blood cells and platelet analog.
5. Add a predetermined amount of NRBC analog prepared in Example 1 or 2 into the suspension medium containing the stabilized human red blood cells, platelet analog and white blood cell component.
6. Mixing the reference control composition formed in step 5. The cell concentration of the red blood cell, white blood cell and platelet components are prepared to simulate the corresponding cell concentrations of a human whole blood sample. The cell concentration of the NRBC analog is prepared to simulate a clinical sample containing a certain level of nucleated red blood cells, preferably in a range of 1 to 50 NRBC per 100 WBC.

EXAMPLE 4

Reference Control Composition Containing a Nucleated Red Blood Cell Component, Multiple White Blood Cell Subpopulation Components and Red Blood Cell and Platelet Components

The procedure for making this reference control composition is essentially the same as the procedure described above in Example 3, except that in step 4 predetermined amounts of multiple white blood cell subpopulation analogs are added into the suspension medium containing the stabilized human red blood cells and platelet analog.

The multiple white blood cell subpopulation analogs are prepared following the procedures described in U.S. Pat. Nos. 4,704,364, 5,320,964 and 5,512,485. Using the multiple white blood cell subpopulation analogs prepared following the procedures described in U.S. Pat. No. 4,704,364, the control composition can be used for nucleated red blood cell measurement and differentiation of white blood cells into three subpopulations. Using the multiple white blood cell subpopulation analogs prepared following the procedures described in U.S. Pat. Nos. 5,320,964 and 5,512,485, the reference control composition can be used for nucleated red blood cell measurement and differentiation of white blood cells into five subpopulations.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A cell treatment composition for altering a nucleus property comprising:
  (a) a conditioning component;
  (b) a lytic component comprising a quaternary ammonium surfactant in an amount enabling permeating cell membrane and reducing a size of a blood cell to substantially a size of cell nucleus thereof; said quaternary ammonium surfactant being represented by following molecular structure:

wherein $R_1$ is an alkyl, alkenyl or alkynyl group having 12 to 16 carbon atoms: $R_2$, $R_3$ and $R_4$ are alkyl groups having 1 to 4 carbon atoms and $X^-$ is chloride or bromide anion; and
  (c) a fixing component for preserving said cell nucleus; wherein said conditioning component, said lytic component, and said fixing component are present at predetermined respective concentrations to alter a nucleus property from a natural value to a target value upon contacting with said cell nucleus.

2. The cell treatment composition of claim 1, wherein said conditioning component comprises a buffer, and an osmolality adjusting agent.

3. The cell treatment composition of claim 1 further comprising an ethoxylated alkyl phenol having an alkyl group with 6 to 12 carbon atoms, and between about 10 to about 50 ethylene oxide groups.

4. The cell treatment composition of claim 3 further comprising an ethoxylated alkyl alcohol represented by following molecular structure:

wherein $R_1$ is an alkyl, alkenyl or alkynyl group having 10 to 22 carbon atoms, $R_2$ is —O—, and n is between 20 and 35.

5. The cell treatment composition of claim 1, wherein said fixing component is a fixative comprising aldehyde.

6. The cell treatment composition of claim 1, wherein said fixing component is a fixative comprising oxazolidine.

7. The cell treatment composition of claim 1, wherein said fixing component is a fixative comprising cyclic urea.

* * * * *